(12) United States Patent
Qiu et al.

(10) Patent No.: US 12,122,754 B2
(45) Date of Patent: Oct. 22, 2024

(54) RELATED SUBSTANCE OF LINAGLIPTIN INTERMEDIATE AND SYNTHESIS METHOD THEREOF

(71) Applicant: WISDOM PHARMACEUTICAL CO., LTD, Nantong (CN)

(72) Inventors: Xiaolong Qiu, Nantong (CN); Hu Wang, Nantong (CN); Tao Xu, Nantong (CN); Lin Hu, Nantong (CN); Ping Zou, Nantong (CN); Zhiwei Zuo, Nantong (CN); Wenbo Liu, Nantong (CN); Lingling Chu, Nantong (CN)

(73) Assignee: WISDOM PHARMACEUTICAL CO., LTD, Nantong (CN)

( * ) Notice: Subject to any disclaimer, the term of this patent is extended or adjusted under 35 U.S.C. 154(b) by 677 days.

(21) Appl. No.: 17/433,618

(22) PCT Filed: Jun. 9, 2021

(86) PCT No.: PCT/CN2021/099081
§ 371 (c)(1),
(2) Date: Aug. 25, 2021

(87) PCT Pub. No.: WO2022/134488
PCT Pub. Date: Jun. 30, 2022

(65) Prior Publication Data
US 2023/0010367 A1    Jan. 12, 2023

(30) Foreign Application Priority Data

Dec. 22, 2020 (CN) .......................... 202011534965.0

(51) Int. Cl.
*C07D 239/74* (2006.01)
(52) U.S. Cl.
CPC ................ *C07D 239/74* (2013.01)

(58) Field of Classification Search
CPC ...................................................... C07D 239/74
USPC .......................................................... 544/283
See application file for complete search history.

(56) References Cited

U.S. PATENT DOCUMENTS

2009/0192314 A1    7/2009  Pfrengle et al.

FOREIGN PATENT DOCUMENTS

| CN | 111285876 A | 6/2020 |
| CN | 112592320 A | 4/2021 |

OTHER PUBLICATIONS

Preparation of (R)-8-(3-amino-piperidin-1-yl)-7-(but-2-ynyl)-3-methyl-1-(4-methyl-quinazolin-2-ylmethyl)-3,7-dihydro-purine-2,6-dione, ip.com, 2014.

Jia-Jia Jin, et al., Brønsted acid catalyzed synthesis of 1,3-di(2-quinolyl) propane derivatives via tandem C(sp3)-H functionalization, Tetrahedron, 2013, pp. 6579-6584, vol. 69.

*Primary Examiner* — Taofiq A Solola
(74) *Attorney, Agent, or Firm* — Bayramoglu Law Offices LLC

(57) ABSTRACT

A related substance of linagliptin intermediate 2-(chloromethyl)-4-methylquinazoline, 4,4'-(2-methylpropane-1,3-diyl)bis(2-chloromethyl)quinazoline) and a method for synthesizing the related substance (impurity) by reacting 2-(chloromethyl)-4-methylquinazoline with acetaldehyde under an alkaline condition and a purification method are provided. The preparation method is simple and convenient to operate, short in reaction time, high in product purity, and high in yield. The synthesized related substance can be used for qualitative and quantitative analysis of the linagliptin intermediate 2-(chloromethyl)-4-methylquinazoline and API impurities of linagliptin, so that the medication safety of the linagliptin is improved.

2 Claims, 2 Drawing Sheets

RELATED SUBSTANCE OF LINAGLIPTIN INTERMEDIATE AND SYNTHESIS METHOD THEREOF

CROSS REFERENCE TO THE RELATED APPLICATIONS

This application is the national phase entry of International Application No. PCT/CN2021/099081, filed on Jun. 9, 2021, which is based upon and claims priority to Chinese Patent Application No. 202011534965.0, filed on Dec. 22, 2020, the entire contents of which are incorporated herein by reference.

TECHNICAL FIELD

The present disclosure belongs to the field of medical technology and drug synthesis, and more specifically relates to a related substance of linagliptin intermediate 2-(chloromethyl)-4-methylquinazoline (the related substance is also referred to as an impurity) and a preparation method thereof, and use of the related substance as a quality control standard for the linagliptin intermediate 2-(chloromethyl)-4-methylquinazoline and linagliptin products.

BACKGROUND

Linagliptin is a novel diabetes medication developed by Boehringer Ingelheim Pharmaceuticals, Inc. and was approved by the US FDA in 2011. It has a very significant effect on reducing blood sugar, without affecting the patient's body weight or increasing the risk of hypoglycemia.

2-(Chloromethyl)-4-methylquinazoline is an important intermediate in the synthesis of linagliptin. Currently, there are three publicly reported synthesis processes: 1) condensing 2-aminoacetophenone and hydroxylamine hydrochloride as starting materials to obtain 1-(2-aminophenyl)-1-ethanone oxime, and cyclizing the 1-(2-aminophenyl)-1-ethanone oxime with chloracetyl chloride to obtain 2-(chloromethyl)-4-methylquinazoline-3-oxide, and finally reducing by phosphorus trichloride to obtain a final product 2-(chloromethyl)-4-methylquinazoline; 2) reacting 5-methyl 1H-benzo[E] [1,4]diazepine-2 (3H)-one as a starting material with phosphorus oxychloride to prepare 2-(chloromethyl)-4-methylquinisoline; and using 3) 2-aminoacetophenone and chloroacetonitrile as starting materials, synthesizing 2-(chloromethyl)-4-methylquinisoline by catalytic ring closure with hydrogen chloride. Among them, the first two synthesis methods use highly toxic materials (phosphorus trichloride and phosphorus oxychloride), which goes against safe production, and leads to high cost of raw materials and low yield of synthetic products. The third synthesis method has a short synthetic route and high yield and is convenient for workshop production. The reaction formula of the third synthesis method is as follows:

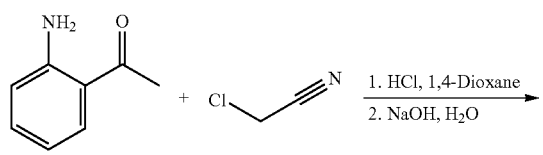

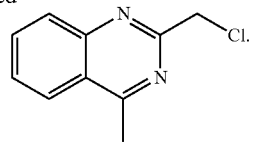

Any substances that affect the purity of the drug are collectively referred to as impurities or related substances of the drug. Impurity research is an important part of drug research and development, which includes the selection of appropriate analytical methods, the accurate distinguishment and determination of the content of impurities, and the determination of the reasonable limits of impurities based on the results of pharmaceutical, toxicological and clinical studies. This research runs through the entire process of drug development and research. The impurities in drugs are generally divided into three categories according to physical and chemical properties thereof, including: organic impurities, inorganic impurities, and residual solvents. Impurities can be divided into process impurities (including unreacted reactants and reagents, intermediates, by-products, and the like), degradation products, and impurities mixed from reactants and reagents according to sources thereof. Impurities can be divided into toxic impurities and ordinary impurities according to toxicity thereof. Impurities can further be classified according to chemical structures thereof, such as steroids, alkaloids, geometric isomers, optical isomers, and polymers. Organic impurities include impurities and degradation products introduced in the process, which may be known or unknown, volatile or non-volatile. Since the chemical structures of such impurities are generally similar to or related to those of active pharmaceutical ingredients, the impurities can usually be referred to as related substances.

The drug impurity detection and analysis method should be sensitive and exclusive. Impurities with different structures are separated and detected by appropriate analytical techniques, so as to achieve effective control of impurities. As separation and detection techniques are developed and updated, and a rapid and efficient separation technique is combined with sensitive, stable, accurate and applicable detection methods, almost all organic impurities can be well separated and detected under suitable conditions. According to the quality standards, the currently commonly used impurity detection methods mainly include high performance liquid chromatography (HPLC), thin layer chromatography (TLC), gas chromatography (GC), and capillary electrophoresis (CE). In recent years, mass spectrometry has been widely used in drug impurity analysis. Gas chromatography combined technology and liquid chromatography combined technology have become important means for drug impurity analysis.

SUMMARY

To better control the quality of 2-(chloromethyl)-4-methylquinazoline and bulk drug of linagliptin, the present disclosure studies impurities in 2-(chloromethyl)-4-methylquinazoline, and discovers an impurity with a new structure-4,4'-(2-methylpropane-1,3-diyl)bis(2-(chloromethyl) quinazoline) (formula I); meanwhile, the present disclosure further provides a synthesis method and a purification method of the impurity. The impurity compound shown in formula I synthesized in the present disclosure is used as an impurity reference substance, which can be used in the quality analysis of the 2-(chloromethyl)-4-methylquinazoline and the bulk drug of linagliptin, and can provide a reference for the selection of process conditions and be conducive to the control of product and drug quality in the production process.

The present disclosure adopts the following technical solutions:

An impurity compound of 2-(chloromethyl)-4-methylquinazoline discovered in the present disclosure has the following structure:

Formula I

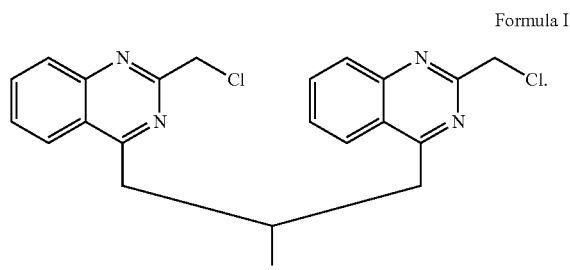 [SMILES: CC(Cc1nc(CCl)nc2ccccc12)Cc1nc(CCl)nc2ccccc12]

The present disclosure further provides a synthesis method of the foregoing compound (formula I), where the method includes using 2-(chloromethyl)-4-methylquinazoline as a starting material to react with acetaldehyde under alkaline conditions to obtain an impurity compound (formula I). The synthetic route is as follows:

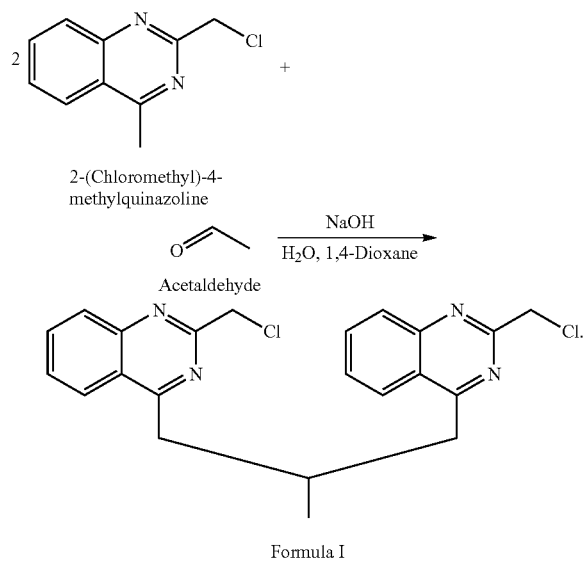

A technical solution of the present disclosure is a preparation method of a high-purity impurity (formula I), where 2-(chloromethyl)-4-methylquinazoline is used as a raw material to undergo coupling reaction with acetaldehyde under alkaline conditions to produce the impurity (formula I).

The method includes the following steps:
fully dissolving 2-(chloromethyl)-4-methylquinazoline and 1,4-dioxane under stirring, to obtain a mixture I;
adding a 30% aqueous sodium hydroxide solution to the mixture I at a controlled temperature of 10-25° C., to obtain a mixture II;
controlling the temperature at 10-25° C., slowly adding acetaldehyde dropwise to the mixture II and reacting for 16 h under stirring at a controlled temperature of 10-25° C., to obtain a mixture III;
after completing the reaction in step 3, adding water to the mixture III, stirring, filtering, and vacuum-drying a filter cake to obtain a yellow solid, namely, a crude product of an impurity shown in formula I; and
fully dissolving the crude product obtained in step 4 in dichloromethane, passing the dichloromethane through a short silica gel column, concentrating a filtrate to dryness, pulping with methyl tert-butyl ether (MBTE), filtering, and vacuum-drying a filter cake to obtain an off-white solid, namely, the impurity shown in formula I.

The present disclosure sets forth an impurity of 2-(chloromethyl)-4-methylquinazoline, and there is no report on the impurity and synthesis method thereof in the existing literature and patents. In the present disclosure, 2-(chloromethyl)-4-methylquinazoline is used as a raw material and 1,4-dioxane and water are used as solvents to undergo coupling reaction with acetaldehyde under alkaline conditions to prepare the impurity.

The present disclosure has the following beneficial effects: The preparation method of the present disclosure is simple and convenient to operate, short in reaction time, simple in purification steps, high in product purity, high in yield, and suitable for industrial production. The synthesized impurities may be used for qualitative and quantitative impurity analysis, thereby improving the quality and medication safety of the bulk drug of linagliptin.

DETAILED DESCRIPTION OF THE EMBODIMENTS

Figure 1A:
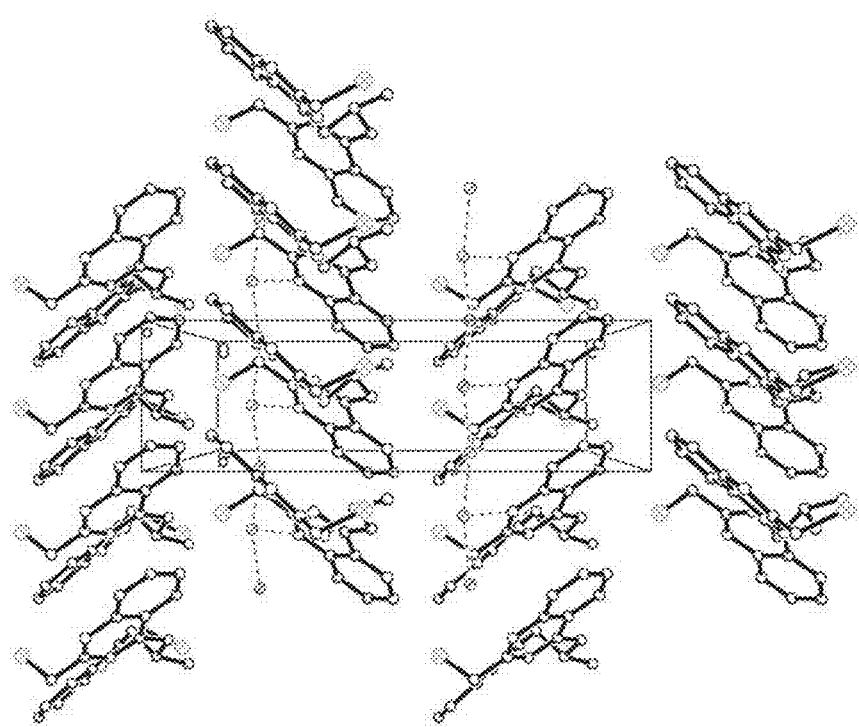
FIG. 1A is a single crystal culture of the impurity shown in formula I.

It should be understood that, based on the disclosure provided herein, those skilled in the art can make various modifications and improvements to the present disclosure without departing from the spirit and scope of the present disclosure. They should fall within the scope of patent protection defined by the claims of this application. In addition, it should be understood that the examples provided herein are only intended to illustrate the present disclosure, and should not be construed as limiting the present disclosure.

The present disclosure will be further described in detail below in conjunction with specific examples.

Example 1

2-(Chloromethyl)-4-methylquinazoline (10.0 g, 51.91 mmol) and 1,4-dioxane (50.0 mL) solution were added into a reaction flask, and stirred until fully dissolved; a 30% aqueous sodium hydroxide solution (50.0 mL) was slowly added at 10-25° C., and acetaldehyde (22.87 g, 519.09 mmol) was slowly added dropwise at 10-25° C., and the reaction was conducted for 16 h under stirring at a controlled temperature of 10-25° C.; water (300 mL) was slowly added, the temperature was controlled at 10-25° C., and the reaction was conducted for 1.5 h, filtered, and vacuum dried at 50° C. to obtain a yellow solid, namely 2.7 g of crude product of an impurity shown in formula I, with a molar yield of 25.29%.

Example 2

2.7 g of crude product of an impurity shown in formula I was added to the reaction flask, and stirred with dichloromethane (50.0 mL) until fully dissolved; the mixture was passed through a short silica gel column (5.0 g). The filtrate was evaporated to dryness under reduced pressure at 40° C., and stirred with MBTE (10.0 mL) at 25° C. for 30 min, and filtered; the resulting solid was vacuum dried at 50° C. to obtain an off-white solid, namely, 2.1 g of pure impurity shown in formula I, with a yield 77.78%.

The molecular formula of the impurity shown in formula I was: $C_{22}H_{20}Cl_2N_4$; m/z: 410.11

The characterization data of the impurity shown in formula I are as follows:
1. Mass spectrum data MS (ESI-Pos): $[M+H]^+$=411.11;
2. Nuclear magnetic instrument model: BRUKER 400 MHZ;

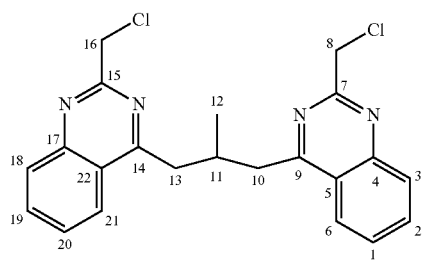 [SMILES: CC(Cc1nc(CCl)nc2ccccc12)Cc1nc(CCl)nc2ccccc12]

The $^1$H-NMR spectrum attribution of the hydrogen spectrum data is as follows

| Chemical shift (ppm) | Number of hydrogen atoms | Peak splitting | Attribution |
| --- | --- | --- | --- |
| 1.12-1.15 | 2 | d (J = 6.0 Hz) | 12 |
| 3.21-3.26 | 3 | m | 10, 11, 13 |
| 3.35-3.62 | 2 | m | 8, 16 |
| 4.79 | 4 | s | 8, 16 |
| 7.65-7.70 | 2 | t (J = 7.2 Hz) | 1, 20 |
| 7.88-7.92 | 2 | t (J = 7.2 Hz) | 2, 19 |
| 8.02-8.05 | 2 | d (J = 8.4 Hz) | 6, 21 |
| 8.26-8.28 | 2 | d (J = 8.4 Hz) | 3, 18 |

The $^{13}$C-NMR spectrum attribution is as follows.

| Chemical shift (δ ppm) | Attribution |
| --- | --- |
| 20.57 | 12 |
| 32.32 | 11 |
| 41.49 | 10, 13 |
| 47.87 | 8, 16 |
| 122.86 | 5, 22 |
| 125.01 | 6, 21 |
| 128.03 | 1, 20 |
| 129.09 | 3, 18 |
| 134.01 | 2, 19 |
| 150.16 | 4, 17 |
| 160.85 | 9, 14 |
| 171.26 | 7, 15 |

Figure 1B:
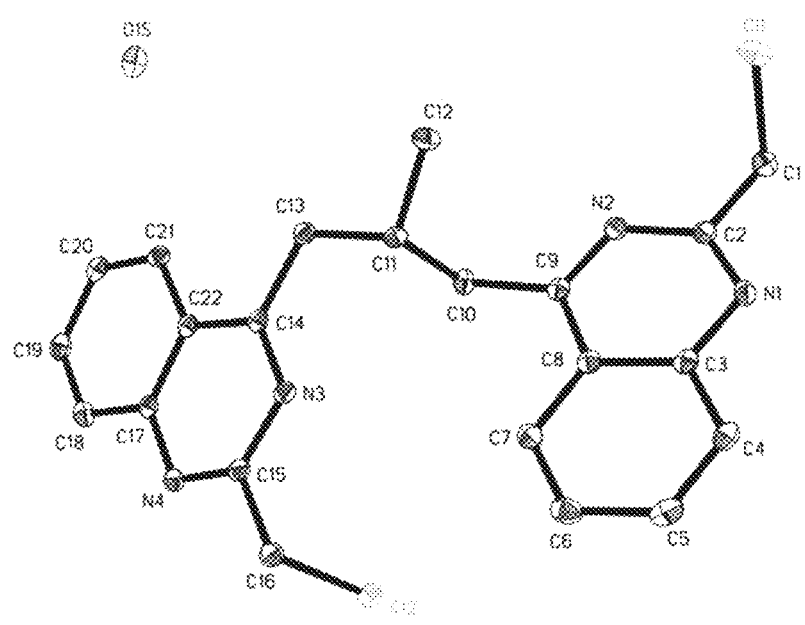
FIG. 1B is the chemical structure of the impurity shown in formula I determined by diffraction of single crystal structures.

3. The chemical structure of the impurity shown in formula I was further determined by single crystal culture and diffraction of single crystal structures, as shown in FIG. 1A and FIG. 1B.

What is claimed is:

1. A related substance of linagliptin intermediate 2-(chloromethyl)-4-methylquinazoline, being 4,4'-(2-methylpropane-1,3-diyl)bis(2-(chloromethyl)quinazoline) (formula I), wherein the related substance has the following chemical structure:

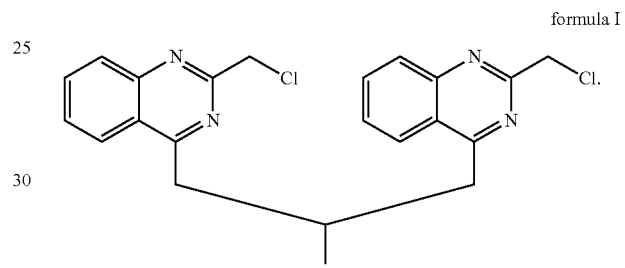

formula I

2. A preparation method of 4,4'-(2-methylpropane-1,3-diyl)bis(2-(chloromethyl)quinazoline) (formula I), comprising the following steps:
(1) fully dissolving 2-(chloromethyl)-4-methylquinazoline and 1,4-dioxane under stirring to obtain a first mixture;
(2) adding a 30% aqueous sodium hydroxide solution to the first mixture at a controlled temperature of 10-25° C. to obtain a second mixture;
(3) controlling the temperature at 10-25° C., slowly adding acetaldehyde dropwise to the second mixture, and reacting for 16 h under stirring at a controlled temperature of 10-25° C. to obtain a third mixture;
(4) adding water to the third mixture, stirring, filtering to obtain a first filter cake, and vacuum-drying the first filter cake to obtain a crude product of an impurity shown in formula I; and
(5) fully dissolving the crude product obtained in step (4) in dichloromethane, passing the dichloromethane through a short silica gel column, concentrating a filtrate to dryness, pulping with methyl tert-butyl ether (MBTE), filtering to obtain a second filter cake, and vacuum-drying the second filter cake to obtain the impurity shown in formula I.

* * * * *